United States Patent [19]

Gunther et al.

[11] 4,234,645
[45] Nov. 18, 1980

[54] PHARMACEUTICAL COMPOSITION

[75] Inventors: Harald Gunther; Herbert C. Fleisch, both of Bern, Switzerland

[73] Assignee: The Procter & Gamble Company, Cincinnati, Ohio

[21] Appl. No.: 931,072

[22] Filed: Aug. 4, 1978

Related U.S. Application Data

[63] Continuation of Ser. No. 782,580, Mar. 29, 1977, abandoned.

[51] Int. Cl.² ............................................. A61K 31/66
[52] U.S. Cl. .................................................. 424/204
[58] Field of Search .......................................... 424/204

[56] References Cited

U.S. PATENT DOCUMENTS

| | | | |
|---|---|---|---|
| 3,553,314 | 6/1971 | Frances | 424/204 |
| 3,553,315 | 6/1971 | Frances | 424/204 |
| 3,584,124 | 6/1971 | Frances | 424/204 |
| 3,584,125 | 6/1971 | Frances | 424/204 |
| 3,641,246 | 2/1972 | Frances | 424/204 |
| 3,662,066 | 5/1972 | Frances | 424/204 |
| 3,678,164 | 7/1972 | Frances | 424/204 |
| 3,683,080 | 8/1972 | Frances | 424/204 |
| 3,962,433 | 6/1976 | Worms | 424/204 |

*Primary Examiner*—Stanley J. Friedman
*Attorney, Agent, or Firm*—Jerry J. Yetter; Donald E. Hasse; Richard C. Witte

[57] ABSTRACT

Dichloromethane diphosphonates affect the biosynthesis of collagen.

6 Claims, No Drawings

PHARMACEUTICAL COMPOSITION

This is a continuation, of application Ser. No. 782,580, filed Mar. 29, 1977, now abandoned.

BACKGROUND OF THE INVENTION

The present invention relates to compositions and processes for affecting the biosynthesis of collagen. More specifically, dichloromethane diphosphonate ($Cl_2MDP$) compounds are administered to humans and lower animals to desirably influence the biosynthesis of collagen.

As is well documented in the literature, many disease states affect collagen and collagen biosynthesis. The introductory portion of the ANNALS OF THE NEW YORK ACADEMY OF SCIENCES, Vol. 86, Art. #4, pages 875-1132 "Connective Tissue and Diseases of Connective Tissue" (1960) collectively considers diseases involving connective tissue, including fiber formation and wound healing, under the term "collagen diseases". Collagen diseases include, for example, rheumatoid arthritis, osteoarthritis, alkylosing spondylitis, rheumatic fever, systemic lupus, and the like.

By the present invention, dichloromethane diphosphonate compounds are used in the treatment of collagen diseases.

DISCUSSION OF RELATED REFERENCES

Various phosphonate compounds are reported in the literature as being useful in the treatment of anomalous mobilization and deposition of calcium phosphate salts (bone mineral) in humans and other animals. See especially the U.S. Pat. Nos. of M. D. Francis: 3,678,164, granted July 18, 1972; 3,662,066, granted May 9, 1972; 3,553,314, granted Jan. 5, 1971; 3,553,315, granted Jan. 5, 1971; 3,584,124, granted June 8, 1971; 3,584,125, granted June 8, 1971; 3,641,246, granted Feb. 8, 1972; as well as German DT No. 2360-798 (June 26, 1975); German DT No. 2343-146 (Mar. 6, 1975); and Belgian BE 822-929 (Dec. 6, 1973).

Attention is directed to U.S. Pat. No. 3,683,080, to M. D. Francis, issued Aug. 8, 1972, wherein the compound $Cl_2MDP$ is one of the phosphonate materials disclosed for use in the treatment of anomalous calcification involving soft tissues and arthritic conditions.

In contrast with the prior art disclosures of the use of various phosphonate materials to prevent the formation of anomalous, calcified mineral deposits in bones, joints and soft tissues, the present invention is based on the new discovery that $Cl_2MDP$ uniquely and importantly affects the biosynthesis of collagen.

SUMMARY OF THE INVENTION

The present invention encompasses a method for treating collagen diseases in humans and lower animals comprising administering to a human or lower animal in need of such treatment a safe and effective amount of a pharmaceutically-acceptable dichloromethane diphosphonate compound of the type described more fully hereinafter.

By the practice of this invention, disease states involving abnormalities or progressive destruction of the body's normal levels of collagen, e.g., at joints, between vertebrae, and the like, are effectively treated. Moreover, the ability of wounds to heal is also desirably enhanced by the $Cl_2MDP$ compounds and the term "wound healing" is encompassed by the generic term "collagen disease".

DETAILED DESCRIPTION OF THE INVENTION

The treatment regimens of this invention employ a safe and effective amount of a pharmaceutically-acceptable dichloromethane diphosphonate compound. These compounds are administered to treat collagen diseases in humans and lower animals in need of such treatment. The dichloromethane diphosphonates herein are conveniently abbreviated as "$Cl_2MDP$".

By "safe and effective amount of $Cl_2MDP$ compound" herein is meant sufficient $Cl_2MDP$ compound to desirably affect and enhance the biosynthesis of collagen, at a reasonable benefit/risk ratio attendant with any medical treatment. Within the scope of sound medical judgment, the dosage of $Cl_2MDP$ compound will vary with the particular condition being treated, the severity of the condition, the duration of the treatment, the specific $Cl_2MDP$ compound employed, and like considerations discussed more fully hereinafter.

By "pharmaceutically-acceptable" herein is meant that the $Cl_2MDP$ drug compound and other ingredients used in the compositions employed herein are suitable for use in contact with the tissues of humans and lower animals without undue toxicity, irritation, allergic response, and the like, commensurate with a reasonable benefit/risk ratio.

The term "administration" of the $Cl_2MDP$ compounds and compositions herein includes systemic use, as by injection (especially parenterally), intravenous infusion, suppositories and oral administration thereof, as well as topical application of the compounds and compositions to an afflicted situs.

By "topical application" herein is meant directly laying on or spreading the $Cl_2MDP$ compounds and compositions on epidermal tissue (including outer skin and oral, gingival, nasal, etc., tissue).

By "afflicted situs" herein is meant a localized area undergoing collagen biosynthesis, especially a wound and the immediate surrounding area.

By the term "comprising" as used herein is meant that various other, compatible drugs and medicaments, as well as inert ingredients, can be conjointly employed in the compositions and processes of this invention, as long as the critical $Cl_2MDP$ compounds are used in the manner disclosed. The term "comprising" thus encompasses and includes the more restrictive terms "consisting of" and "consisting essentially of" which characterize the use of the essential $Cl_2MDP$ compounds in the practice of this invention.

By "compatible" herein is meant that the components of the compositions which can be used in the practice of this invention are capable of being commingled without interacting in a manner which would substantially decrease the efficacy of the $Cl_2MDP$ compositions under ordinary use situations.

All percentages herein are by weight, unless otherwise specified.

The $Cl_2MDP$ compounds used in the practice of this invention are of the formula

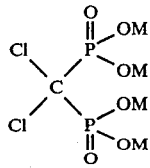

where M is hydrogen, a pharmaceutically-acceptable cation, e.g., alkali metal, especially Na or K, or an alkyl or aryl moiety, e.g., methyl, ethyl, propyl, butyl, phenyl, or the like.

The dichloromethane diphosphonates can be prepared in the manner described in ORGANIC PHOSPHORUS COMPOUNDS Vol. 7, Kosolapoff and Maier (1976) page 258 (citing references). In general, the reaction sequence for the preparation of $Cl_2MDP$ compounds involves an Arbuzov-type rearrangement of dibromomethane with triisopropyl phosphite, followed by chlorination and acidulation to prepare the $Cl_2MDP$, free acid form. The acid form can be neutralised with any desired (pharmaceutically-acceptable) base or can be esterified, to provide $Cl_2MDP$ compounds for use in the practice of this invention.

The following experiments demonstrate the heretofore unsuspected utility of $Cl_2MDP$ for desirably affecting the biosynthesis of collagen. In the experiments, the term "NMRI" means an inbred strain of mice obtained from the MRC Laboratory Animal Centre, Carshalton, Surrey, England; the term "SDS" means sodium dodecyl sulfate; the term "βAPN" means β-aminopropionitrile; "EHDP" means disodium ethane-1-hydroxy-1,1-diphosphonate; the meanings of all other terms and abbreviations are defined or are apparent from the text.

Materials and Methods

A. Organ Culture

One-day old NMRI mice or Wistar rats (bred in our Institute) were injected daily with EHDP or $Cl_2MDP$ in concentrations of 1 and 10 mg P/kg of body weight. The two diphosphonates were dissolved in normal saline and administered s.c. The control animals received equivalent volumes of saline. Body weights were determined every day prior to the injections. The animals were fed ad libitum with Altromin Laboratory chow (Switzerland). After eight days the mice or rats were sacrificed by decapitation after which calvariae and tibiae were excised and immediately placed in Minimum Essential Medium (Gibco) until all explants were dissected. The tissues were then washed three times with MEM after which new medium was added (4 ml/10 explants) containing 50 μCi/ml $^3$H-proline, 100 μg/ml ascorbic acid, 10% fetal calf serum and 1 mM beta aminopropionitril, but no diphosphonates. After 18 hours of incubation at 37° C. and in a gas atmosphere of 5% $CO_2$ and 95% air, the explants were taken from the medium and washed three times with 5 ml cold deionized water containing 1 mg/ml cold proline.

Isolation of Collagen

The washed bones were carefully cleaned from facia and adhering cell and cell debris. In the case of the tibiae, the cartilaginous heads were separated from the shafts and the bone marrow was removed using a syringe equipped with a fine injection needle. The tibia heads from these nine-day old animals are not yet mineralized and represent pure cartilage. From this point, three tissues—calvaria (lamellar bone), tibia (cortical bone) and tibia heads (epiphyseal cartilage)—were processed separately. All three tissues were then pulverized under liquid nitrogen and the resulting bone and cartilage powders were freeze dried until a stable dry weight was obtained. Aliquots of the dried powder were hydrolyzed in 6 N HCl for 18 hours at 180° C. and hydroxyproline and calcium determinations were run to establish the collagen content and the degree of mineralization of the starting materials.

Acetic Acid Extraction

The main portion of the tissue powders were then subjected to 0.5 M acetic acid (10 mg/ml) treatment for 48 hours at 4° C. which effectively demineralized the samples and extracted the acid soluble collagen. Extract and acetic acid-insoluble residues were separated by centrifugation (10,000×g). The supernatant was then divided into two halves of which one part was used to determine the amount of collagen which was dissolved by acetic acid and the other one was processed for the determination of the radioactivity which was incorporated into newly-synthesized collagen. The degree of solubilization of the collagen was determined after hydrolysis of the undialyzed acetic acid extract in 6 N HCl and a subsequent hydroxyproline determination according to a modified method by Stegemann with an automatic Technicon analyzer. To assess the incorporation of $^3$H-proline into the collagen molecule the acetic acid extract was dialyzed extensively against 0.5 M and 0.1 M acetic acid to remove free contaminating $^3$H-proline counts. To assure a quantitative recovery of radioactive collagen which may stick to the walls of the dialyzing tubing, cold acid-soluble rat or mouse skin collagen in a concentration of 1 mg/ml was added. The radioactivity was determined with a Packard TriCarb scintillation counter.

Pepsin Extraction

The residues from the acetic acid extraction step were treated with pepsin which was dissolved in 0.5 M acetic acid in a concentration of 1 mg/ml. The extraction was carried out for 24 hours at 4° C. Extract and residue were again separated by centrifugation. As was done with the acetic acid extract, the supernatant was split into two halves, of which one part was hydrolyzed to determine the degree of solubilization of collagen by pepsin; the other half was subjected to an extensive dialysis. However, before the dialysis was started, the pH of the pepsin extract was brought up to pH 7.6 with 1 M NaOH to inactivate the pepsin and neutral salt-soluble rat or mouse skin collagen was added. Dialysis was carried out against 1 M NaCl–0.05 M Tris, pH 7.6.

Determination of Hydroxyproline

After hydrolysis of acid and pepsin-soluble collagen and after evaporation of the HCl the samples were dissolved in 0.1 M citrate buffer, pH 2.9, and applied on a column (0.8×25 cm) packed with Dowex 50w-8×. Separation of the hydroxylated from the non-hydroxylated amino acid was achieved by eluting the columns with the buffer in which the samples were dissolved.

Determination of the Chain Composition of the Collagen

The identification of the chain composition of bone (type I) and cartilage (type II) collagen was achieved by polyacrylamide gel electrophoresis (PAGE) according to Guenther, et al. In short, radioactive-labeled collagen samples were loaded on 5% gels which were prepared with 100 mM Tris-Borate buffer, pH 8.6, containing 0.1% SDS. After completion of the run, monitored with FLURAM ®-tagged collagen, the gels were sliced into 1 mm discs with a gel slicer described by Benya, et al. The gel discs were placed in scintillation vials to which 0.5 ml of a 3% $H_2O_2$ solution was added. The vials were then transferred into a drying oven and kept there for two hours at 60° C. The slices were counted using a scintillation cocktail which contained 10% Triton X-100 to accommodate the 0.5 ml hydrogen peroxide.

Determination of Calcium

The amount of calcium contained in the original tissues was carried out on a Corning calcium Analyzer 940, after the tissue powder was hydrolyzed.

B. Cell Culture

Isolation of Calvariae Cells

Freshly-excised calvariae from two-to three-day old Wistar rats were cleaned from the slimy cell layer and then placed in MEM containing 227 mg/l $NaHCO_3$, antibiotics and 3 mg/ml collagenase. The explants were shaken for two hours in a water bath at 37° C. The resulting suspension was then diluted with fresh MEM and sucked several times in and out of a sterile Pasteur pipette to break up tissue and cell clumps. The suspension was then transferred into sterile test tubes where greater tissue pieces were allowed to settle. The upper 8/10 of the suspension was then taken and centrifuged at 350×g for 7 minutes. The pellets were resuspended in MEM and the separation of big particles was repeated. The final cell pellet was then resuspended in MEM containing 2.2 g/l $NaHCO_3$, 10% fetal calf serum and antibiotics and plated at a density of $1.5 \times 10^5$ cells/dish. The cells were incubated at 37° C. in 5% $CO_2$. Once the cells had attached to the dish, the old medium was drawn off and new medium containing 0.25 M diphosphonate was added. The medium was changed every third day. On the 7th or 8th day the cells reached confluency; fresh medium was then added containing 0.25 mM EHDP or $Cl_2MDP$, 30 μCi $^3H$ proline, 100 μg vitamin C and 1 mM βAPN. After 18 hours of incubation the cell layers were trypsinized.

From the resulting cell suspension first a cell count was performed; then the cells were centrifuged. The supernatant was used for collagen determination as well as for the determination of $^3H$-proline incorporation. The procedure is described under "Isolation of Collagen". The cell pellets were resuspended in a balanced salt solution. One half was used for DNA determination; the other half was used to determine the intracellular newly-synthesized collagen.

Isolation of Ear Cartilage Cells

The isolation of ear chondrocytes and the collagen synthesis study on rabbit ear cartilage was carried out in the same manner as described with the calvariae bone cell study.

Results

Organ Culture

The results presented in this report are from rats only. However, these data represent very adequately the ones obtained from mice. In addition the results listed in Tables I through V are from one diphosphonate concentration only, namely 10 mg P/kg body weight. Concentrations of 1 mg P/kg showed no significant effects as compared with control subjects, at least not during an eight-day treatment of EHDP or $Cl_2MDP$.

The figures in Table I show the collagen and calcium contents of the starting tissue specimens expressed in mg/g tissue. As expected the EHDP-treated animals show a decreased amount Ca within the bone tissue thus reflecting a decrease in mineralization. The $Cl_2MDP$-treated subjects show a comparable degree of mineralization to the control animals. Furthermore it can be seen that the collagen content of EHDP as well as the $Cl_2MDP$ treated tissues show higher collagen values considering the lower mineral content as is the case with the EHDP.

The sequential collagen extraction (Table II) using acetic acid and pepsin containing acetic acid revealed interesting results. The experiments show that EHDP does not alter the total extractability of bone collagen; however, this was not the case in the $Cl_2MDP$-treated test animals where the solubility of bone collagen is drastically increased. The cartilage collagen deviated in this respect; it showed little to no effect with $Cl_2MDP$ but a decrease in the extraction with EHDP.

The incorporation of $^3H$-proline into bone and cartilage collagen of isolated cultured explants showed differences with the diphosphonate-treated rats versus the controls. As can be seen in Table III, isotopically-labeled proline is taken up and incorporated into bone collagen to a much lesser extent by EHDP-treated than control animals.

With $Cl_2MDP$ a remarkable increase in the $^3H$-proline incorporation was observed. As far as cartilage collagen is concerned, EHDP promotes the incorporation of $^3H$-proline to a small extent whereas with $Cl_2MDP$ an augmentation of roughly 700% was calculated.

Cell Culture

Table IV depicts the incorporation of $^3H$-proline into collagen by isolated bone and cartilage cells in culture. As was evident in organ culture, here also the influence of $Cl_2MDP$ is such that an increase in the radioactivity of isolated collagen was found. As seen in Table IVa, a three-fold increase in the synthesis of collagen from ear cartilage chondrocytes was measured.

Finally, no change was evident in the degree of hydroxylation of proline by either diphosphonate. As seen in Table V all values of the ratios of hydroxyproline to proline are well within the normal range. The chain composition of bone collagen consisting of 2 $\alpha_1$ and 1 $\alpha_2$ chains $[\alpha_1(I)]_2\alpha_2$ as well as from cartilage collagen with the chain composition $[\alpha_1(III)]_3$ was not altered (Table V). The values for the chain composition were taken from mouse tissues which showed no difference from rat-derived tissues.

TABLE I

| Collagen and Calcium Content of Cultured Explants (Rats) Before Demineralization and Extraction | | |
|---|---|---|
| | Collagen mg/g | Calcium mg/g |
| Control | | |
| Calvaria | 186.5 ± 3.31 | 232.69 ± 3.53 |
| Tibia | 122.21 ± 11.15 | 182.27 ± 8.12 |
| Cartilage | 156.70 ± 3.36 | 26.17 ± 1.11 |
| EHDP 10 mg P | | |
| Calvaria | 326.3 ± 5.99 | 107.35 ± 4.32 |

TABLE I-continued

Collagen and Calcium Content of Cultured Explants (Rats) Before Demineralization and Extraction

|  | Collagen mg/g | Calcium mg/g |
|---|---|---|
| Tibia | 276.8 ± 5.71 | 103.31 ± 7.83 |
| Cartilage | 249.4 ± 15.71 | 7.57 ± 2.39 |
| $Cl_2MDP$ 10 mg P |  |  |
| Calvaria | 216.5 ± 7.23 | 204.20 ± 6.17 |
| Tibia | 115.7 ± 2.72 | 208.50 ± 5.19 |
| Cartilage | 241.0 ± 14.76 | 16.99 ± 1.99 |

Mean ± SD
Number of experiments 3; 8 to 9 animals/experiment

TABLE II

Sequential Collagen Extraction (Rat)

|  | Acetic Acid mg/g collagen | Pepsin mg/g collagen | Total Extraction mg/g collagen | % Extract. | Δ % to cont. |
|---|---|---|---|---|---|
| Control |  |  |  |  |  |
| Calvaria | 7.15 ± 0.97* | 55.00 ± 4.12 | 62.15 | 6.22 | 100 |
| Tibia | 10.71  1.23 | 60.26  3.77 | 70.97 | 7.10 | 100 |
| Cartilage | 2.99  0.83 | 72.90  6.19 | 75.89 | 7.59 | 100 |
| EHDP 10 mg P |  |  |  |  |  |
| Calvaria | 1.41  0.09 | 64.60  3.98 | 66.01 | 6.60 | 100 |
| Tibia | 4.82  0.75 | 67.28  5.57 | 72.10 | 7.21 | 100 |
| Cartilage | 0.97  0.17 | 26.84  7.11 | 27.81 | 2.78 | 36.3 |
| $Cl_2MDP$ 10 mg P |  |  |  |  |  |
| Calvaria | 16.29  2.17 | 116.88  6.11 | 133.17 | 13.32 | 214.1 |
| Tibia | 11.58  2.01 | 107.39  6.39 | 118.97 | 11.89 | 167.7 |
| Cartilage | 17.23  3.11 | 44.34  7.32 | 61.57 | 6.16 | 81.1 |

*S.D.
Number of experiments 3; 8 to 9 animals/experiment

TABLE III

|  | Organic Matrix* mg Total | $^3$H-Proline Incorporation | | % Incorporation |
|---|---|---|---|---|
|  |  | Total Counts CPM Incorporated | CPM/mg* Organic Matrix |  |
| Control |  |  |  |  |
| Calvaria | 86.06 | 8.68 × $10^5$ | 10.01 × $10^3$ ± 1.20 | 100 |
| Tibia | 91.11 | 3.25 × $10^5$ | 3.57 × $10^3$ ± 0.51 | 100 |
| Cartilage | 85.60 | 1.23 × $10^5$ | 1.44 × $10^3$ ± 0.40 | 100 |
| EHDP 10 mg P |  |  |  |  |
| Calvaria | 70.14 | 4.18 × $10^5$ | 5.96 × $10^3$ ± 0.89 | 59.54 ± 5.31 |
| Tibia | 73.11 | 1.92 × $10^5$ | 2.62 × $10^3$ ± 0.35 | 82.07 ± 6.01 |
| Cartilage | 62.19 | 1.08 × $10^5$ | 1.74 × $10^3$ ± 0.10 | 120.83 ± 3.17 |
| $Cl_2MDP$ 10 mg P |  |  |  |  |
| Calvaria | 72.50 | 17.01 × $10^5$ | 23.46 × $10^3$ ± 3.17 | 234.37 ± 9.77 |
| Tibia | 71.63 | 3.79 × $10^5$ | 5.29 × $10^3$ ± 0.95 | 148.18 ± 11.13 |
| Cartilage | 73.17 | 8.33 × $10^5$ | 11.38 × $10^3$ ± 2.91 | 790.27 ± 89.90 |

Mean ± SD
*Represents organic matrix of explants cultured with $^3$H-proline
Number of experiments 3; 8 to 9 animals/experiment

TABLE IV

Cell Culture Uptake of $^3$H-proline into Collagen*

|  | Total Counts Incorporated CPM | DNA μg | CPM/μg DNA |
|---|---|---|---|
| Rabbit ear cartilage cells |  |  |  |
| Control | 14.41 × $10^4$ | 11.1 | 12.9 × $10^3$ |
| EHDP 0.25 mM | 21.36 × $10^4$ | 13.1 | 16.3 × $10^3$ |
| $Cl_2MDP$ 0.25 mM | 163.14 × $10^4$ | 11.4 | 143.1 × $10^3$ |

|  | Total Counts Incorporated CPM | Number of Cells in mill. | CPM/$10^6$ cells |
|---|---|---|---|
| Rat calvaria isolated cells |  |  |  |
| Control | 4.86 × $10^6$ | 9.96 | 4.88 × $10^5$ |
| EHDP 0.25 mM | 4.69 × $10^6$ | 10.72 | 5.83 × $10^5$ |
| $Cl_2MDP$ 0.25 mM | 6.26 × $10^6$ | 3.64 | 12.89 × $10^5$ |

*Counts given are non-dialyzable, presumably incorporated into collagen.

TABLE IVa*

Incorporation of $^3$H-Proline Synthesis of Collagen by Rabbit Ear Cartilage Chondrocytes

|  | CPM/10 μg DNA | μg coll. synth./ 10 μg DNA | Sp. activity of collagen synthesized |
|---|---|---|---|
| Control | 12.9 × $10^4$ | 2.837 | 4.54 × $10^4$ |
| EHDP 0.25 mM | 16.3 × $10^4$ | 3.992 | 4.08 × $10^4$ |
| $Cl_2MDP$ 0.25 mM | 143.1 × $10^4$ | 7.561 | 18.92 × $10^4$ |

*Values are preliminary and derived from 2 experiments only.

TABLE V

Hydroxylation of Proline to Hydroxyproline

|  | Calvaria | Tibia | Cartilage |
|---|---|---|---|
| Control | 0.77* | 0.76 | 0.73 |
| EHDP | 0.77 | 0.76 | 0.67 |

TABLE V-continued

| Hydroxylation of Proline to Hydroxyproline | | | |
|---|---|---|---|
| $Cl_2MDP$ | 0.76 | 0.77 | 0.75 |

*ratio hydroxyproline/proline

| Ratios of Individual Chains | | | |
|---|---|---|---|
| | Type I Calvaria | Type I Tibia | Type II Cartilage |
| Control | 2.15:1* | 1.96:1 | 8:1 |
| EHDP | 2.34:1 | 1.94:1 | 10:1 |
| $Cl_2MDP$ | 1.91:1 | 2.39:1 | 11.5:1 |

*ratio $\alpha_1/\alpha_2$
Collagens from mouse tissues

PREFERRED MODE

Within the scope of sound medical judgment, the dosage of $Cl_2MDP$ will vary with the particular condition being treated, the severity of the condition, the duration of treatment, and like factors within the specific knowledge and expertise of the attending physician. However, single dosages can typically range from 0.01 to 500 mg per kilogram of body weight, preferably 0.5 to 50 mg/kg (unless otherwise specified, the unit designated "mg/kg" as used herein refers to mg/kg of body weight). The higher dosages within this range are usually required in the case of oral administration because of somewhat limited absorption of the $Cl_2MDP$ through the gut. Up to four dosages per day can be used routinely, but this can be varied to the needs of the patient, consistent with a sound benefit:risk ratio. Dosages greater than about 500 mg/kg may produce untoward symptoms and are usually avoided; moreover, daily dosages greater than about 2,000 mg/kg are not ordinarily required to produce the desired benefit and may produce toxic side effects. Again, however, patient-to-patient variations in response may be expected. Dosages as low as about 0.01 mg/kg are useful, especially if administered intravenously.

Preferably, dosages ranging from about 10 to about 100 mg/kg are employed when the $Cl_2MDP$ is administered orally.

For parenteral administration (s.c., i.p., i.m.), $Cl_2MDP$ dosages are preferably from about 0.5 mg/kg/day to about 20 mg/kg/day. For long-term parenteral infusion (i.v.) the most highly preferred dosage range is from about 1 mg/kg/day to about 5 mg/kg/day.

For purposes of oral administration the $Cl_2MDP$ can be formulated in the form of capsules, tablets or granules. For treatment of non-human animals, the $Cl_2MDP$ is preferably incorporated in animal feed, feed supplements or feed concentrates. $Cl_2MDP$ can also be prepared in unit dosage form together with a pharmaceutical carrier, each unit dosage form containing from ca. 15 mg to 10 g of $Cl_2MDP$. The preferred concentration range of $Cl_2MDP$ in unit dosage forms intended for use by humans and smaller domesticated animals is from 15 mg to 1,000 mg, more preferably 100 mg to 500 mg. A higher concentration range, i.e., from 1 g to 5 g is preferred in unit dosage forms intended for treatment of larger animals such as cattle, horses, etc.

As used herein, the term "pharmaceutical carrier" denotes a solid or liquid filler, diluent or encapsulating substance. Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose, acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents and preservatives, can also be present. Tableting is done using conventional techniques.

The pharmaceutical carrier employed in conjunction with the $Cl_2MDP$ is used at a concentration sufficient to provide a practical size to dosage relationship. Preferably, the pharmaceutical carrier comprises from about 0.1% to 99% by weight of the total composition.

Animal feed compositions to which the $Cl_2MDP$ can be added generally include as feedstuffs a cellulosic roughage component such as hay, straw, plant hulls, corn cobs, etc. Protein-containing components such as whole grains, including corn, wheat, barley, oats, rye, millet and alfalfa are typically included.

The following examples illustrate compositions and methods used in the practice of this invention, but are not intended to be limiting thereof.

EXAMPLE I

Gelatin capsules are prepared by conventional methods, as follows:

| Ingredient | Mg per Capsule |
|---|---|
| $Cl_2MDP$* | 350.00 |
| Starch | 50.00 |

*Mixture of di- and tri-sodium salts

The above capsules administered twice daily substantially enhance collagen biosynthesis in patients in need of such treatment.

The sodium salt form of $Cl_2MDP$ is preferred for use herein. However, the potassium salt form of $Cl_2MDP$ and the $C_1$-$C_4$ alkyl esters of $Cl_2MDP$ can be substituted for the $Cl_2MDP$, sodium salts, in the composition of Example I with good results.

EXAMPLE II

Tablets are prepared by conventional methods, formulated as follows:

| Ingredient | Mg per Tablet |
|---|---|
| $Cl_2MDP$* | 250.00 |
| Lactose | 40.00 |
| Starch | 2.50 |
| Magnesium stearate | 1.00 |

*Disodium salt

The above composition is administered four times daily to a patient weighing approximately 70 kilograms to enhance collagen biosynthesis in a therapeutic regimen to promote wound healing.

The tablets of Example II are administered four times daily to patients afflicted with osteoarthritis, rheumatoid arthritis, alkylosing spondylitis, rheumatic fever or systemic lupus to provide a desirable effect on collagen biosynthesis.

EXAMPLE III

A complete feed composition embodying the present invention and useful in the treatment of joint diseases of animals involving the anomalous metabolism of collagen is as follows:

| Component | Parts by Weight |
|---|---|
| Timothy hay | 960 |
| Dehydrated alfalfa | 40 |
| Yellow corn | 600 |
| Corn starch | 310 |
| Iodized salt | 10 |
| Bone meal | 20 |
| $Cl_2MDP$ (acid form) | 40 |

EXAMPLE IV

Solutions for parenteral administration or topical administration of $Cl_2MDP$ are prepared by dissolving $Cl_2MDP$ (acid form) in water at concentrations of ca. 1%–10% by adjusting the pH to ca. 7.4 with a pharmaceutically-acceptable base corresponding to the desired salt form, and sterilizing the resulting solution by standard sterilization techniques.

The $Cl_2MDP$ solutions prepared in the foregoing manner can be administered parenterally by subcutaneous, intradermal, intramuscular or intravenous injection, or i.v. infusion. The usual, and preferred, dosage ranges by these modes of administration are as follows:

| | |
|---|---|
| Subcutaneous | 0.05–10 mg/kg |
| Intradermal | 0.05–10 mg/kg |
| Intramuscular | 0.05/5 mg/kg |
| Intravenous | 0.05–5 mg/kg |

Solutions of the foregoing type can also be applied directly (topically) to an afflicted situs such as a cut, puncture, abrasion, eruption, wound, or the like, to promote collagen metabolism and to promote healing.

What is claimed is:

1. A method for treating ankylosing spondylitis in humans and lower animals comprising administering to a human or lower animal in need of such treatment a safe and effective amount of a pharmaceutically-acceptable dichloromethane diphosphonate compound selected from the group consisting of dichloromethane diphosphonic acid, salts of dichloromethane diphosphonic acid, and alkyl and aryl esters of dichloromethane diphosphonic acid.

2. A method for treating rheumatic fever in humans and lower animals comprising administering to a human or lower animal in need of such treatment a safe and effective amount of a pharmaceutically-acceptable dichloromethane diphosphonate compound selected from the group consisting of dichloromethane diphosphonic acid, salts of dichloromethane diphosphonic acid, and alkyl and aryl esters of dichloromethane diphosphonic acid.

3. A method for treating systemic lupus in humans and lower animals comprising administering to a human or lower animal in need of such treatment a safe and effective amount of a pharmaceutically-acceptable dichloromethane diphosphonate compound selected from the group consisting of dichloromethane diphosphonic acid, salts of dichloromethane diphosphonic acid, and alkyl and aryl esters of dichloromethane diphosphonic acid.

4. A method for treating wound healing in humans and lower animals comprising administering to a human or lower animal in need of such treatment a safe and effective amount of a pharmaceutically-acceptable dichloromethane diphosphonate compound selected from the group consisting of dichloromethane diphosphonic acid, salts of dichloromethane diphosphonic acid, and alkyl and aryl esters of dichloromethane diphosphonic acid.

5. A method according to claim 4 wherein the dichloromethane diphosphonate compound is applied topically to the afflicted situs of the wound.

6. A method according to claims 1, 2, 3, or 4 wherein the dichloromethane diphosphonate compound comprises the sodium salt form of dichloromethane diphosphonate.

* * * * *